United States Patent
Alesi et al.

(10) Patent No.: US 11,883,041 B2
(45) Date of Patent: Jan. 30, 2024

(54) CATHETER FOR THROMBUS REMOVAL

(71) Applicants: Michael Alesi, Staten Island, NY (US); Edward Cordiano, Keyport, NJ (US)

(72) Inventors: Michael Alesi, Staten Island, NY (US); Edward Cordiano, Keyport, NJ (US)

( * ) Notice: Subject to any disclaimer, the term of this patent is extended or adjusted under 35 U.S.C. 154(b) by 171 days.

(21) Appl. No.: 17/242,827

(22) Filed: Apr. 28, 2021

(65) Prior Publication Data

US 2021/0338255 A1 Nov. 4, 2021

Related U.S. Application Data

(60) Provisional application No. 63/017,773, filed on Apr. 30, 2020.

(51) Int. Cl.
*A61B 17/22* (2006.01)
*A61M 25/00* (2006.01)
*A61M 1/00* (2006.01)

(52) U.S. Cl.
CPC ............... *A61B 17/22* (2013.01); *A61M 1/67* (2021.05); *A61M 1/743* (2021.05); *A61M 1/87* (2021.05); *A61M 25/007* (2013.01); *A61B 2017/22079* (2013.01)

(58) Field of Classification Search
CPC ............... A61M 25/00; A61M 25/008; A61M 25/0043; A61M 25/0067; A61M 25/0068; A61M 25/0071; A61M 2025/006; A61B 17/32; A61B 17/3205; A61B 2018/00315; A61B 2018/00345; A61B 2018/00404; A61B 2018/0041

See application file for complete search history.

(56) References Cited

U.S. PATENT DOCUMENTS

| | | | |
|---|---|---|---|
| 4,391,276 A * | 7/1983 | Lazarus | A61M 1/285 604/266 |
| 5,188,619 A | 2/1993 | Myers | |
| 5,843,050 A | 12/1998 | Jones et al. | |
| 6,749,619 B2 | 6/2004 | Ouriel et al. | |
| 7,323,002 B2 | 1/2008 | Johnson et al. | |
| 8,702,724 B2 | 4/2014 | Olsen et al. | |
| 9,301,829 B2 | 4/2016 | Rauker et al. | |
| 9,844,387 B2 | 12/2017 | Marchand et al. | |
| 10,188,409 B2 | 1/2019 | Smalling | |
| 2002/0169469 A1 * | 11/2002 | Klein | A61M 1/84 606/167 |
| 2005/0148953 A1 | 7/2005 | Fulton, III | |
| 2007/0173784 A1 | 7/2007 | Johansson et al. | |

(Continued)

FOREIGN PATENT DOCUMENTS

WO     WO-9904701 A1 *    2/1999       A61B 17/22

*Primary Examiner* — Leslie Lopez
*Assistant Examiner* — Jihad Dakkak
(74) *Attorney, Agent, or Firm* — Hoffmann & Baron, LLP

(57) ABSTRACT

A catheter, a kit and a method of using the catheter for removing a thrombus from a blood vessel in a mammal. The catheter includes a tubular body with a hollow interior, an exterior surface, a proximal end, and a distal end and a plurality of protrusions extending upwardly from the exterior surface, wherein each protrusion has an aperture. The distal end of the catheter is inserted into the blood vessel and a suction is applied to the proximal end of the catheter to aspirate the thrombus from the blood vessel. The kit includes the catheter, a suction device and a mechanism for controlling the suction flow.

18 Claims, 4 Drawing Sheets

(56) References Cited

U.S. PATENT DOCUMENTS

| | | | |
|---|---|---|---|
| 2013/0138053 A1* | 5/2013 | Shippert | A61M 25/007 604/272 |
| 2018/0064462 A1* | 3/2018 | Walzman | A61B 17/320758 |
| 2018/0207397 A1* | 7/2018 | Look | A61M 1/84 |
| 2018/0236203 A1 | 8/2018 | Franklin et al. | |
| 2018/0289394 A1 | 10/2018 | Shah | |

* cited by examiner

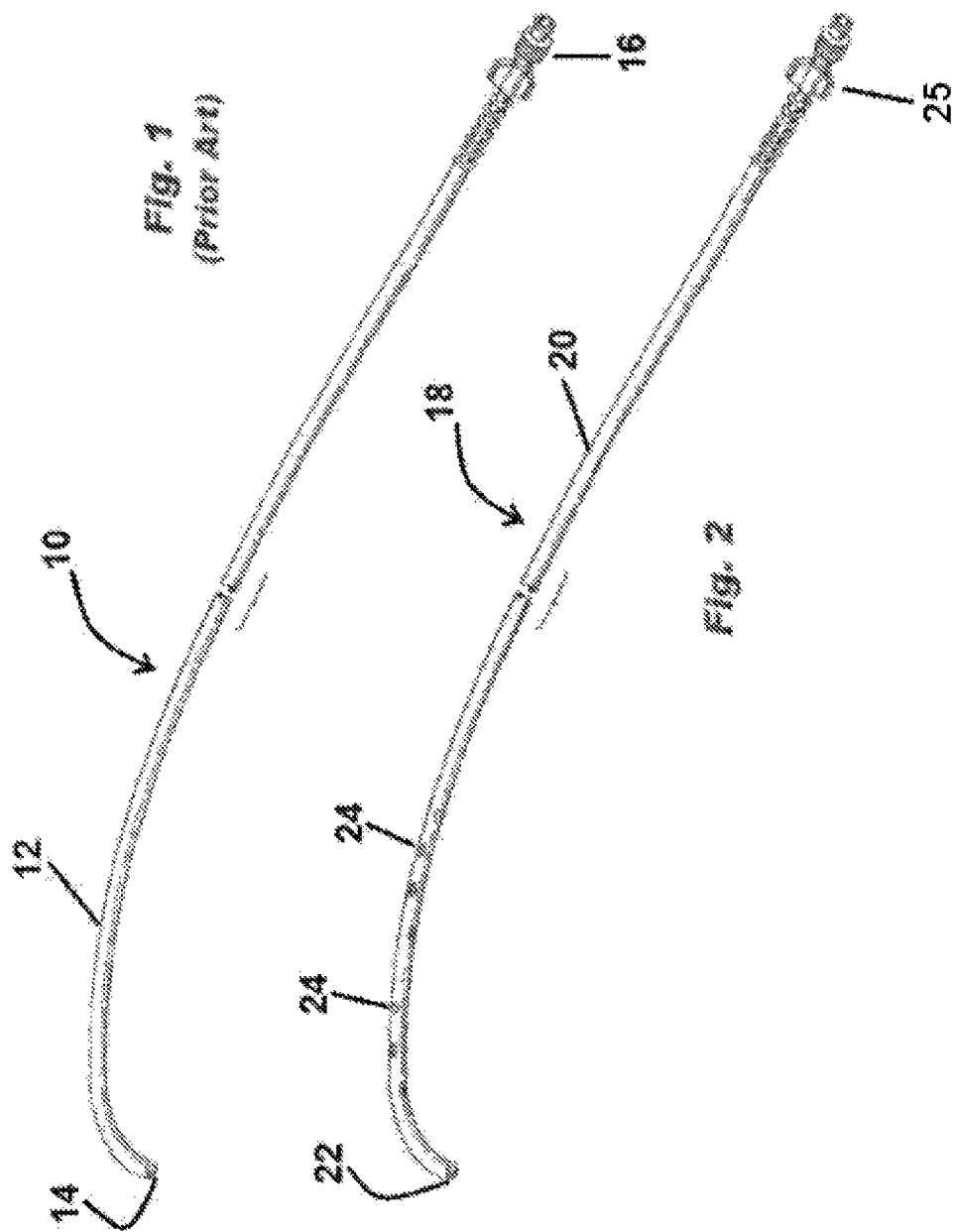

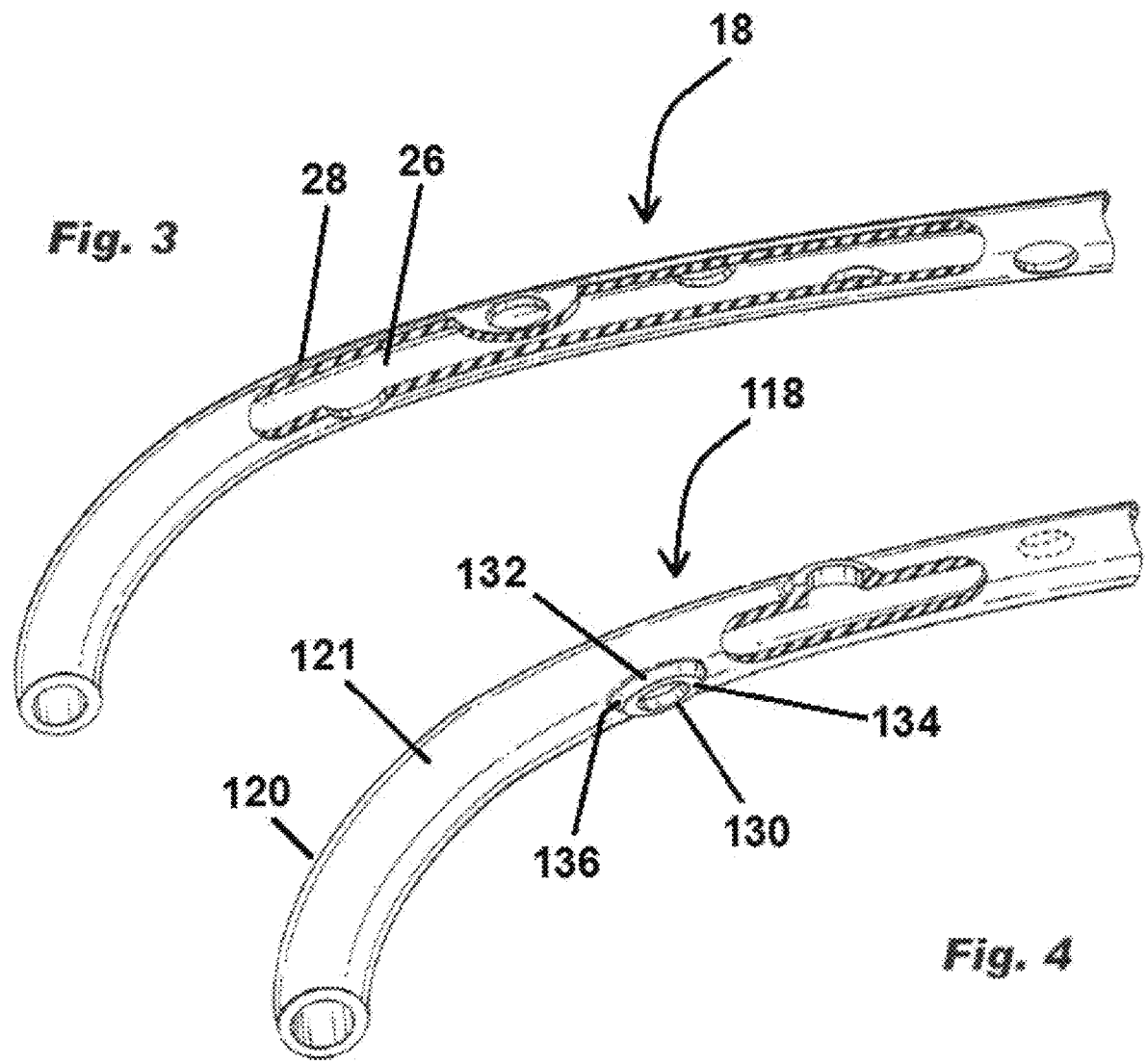

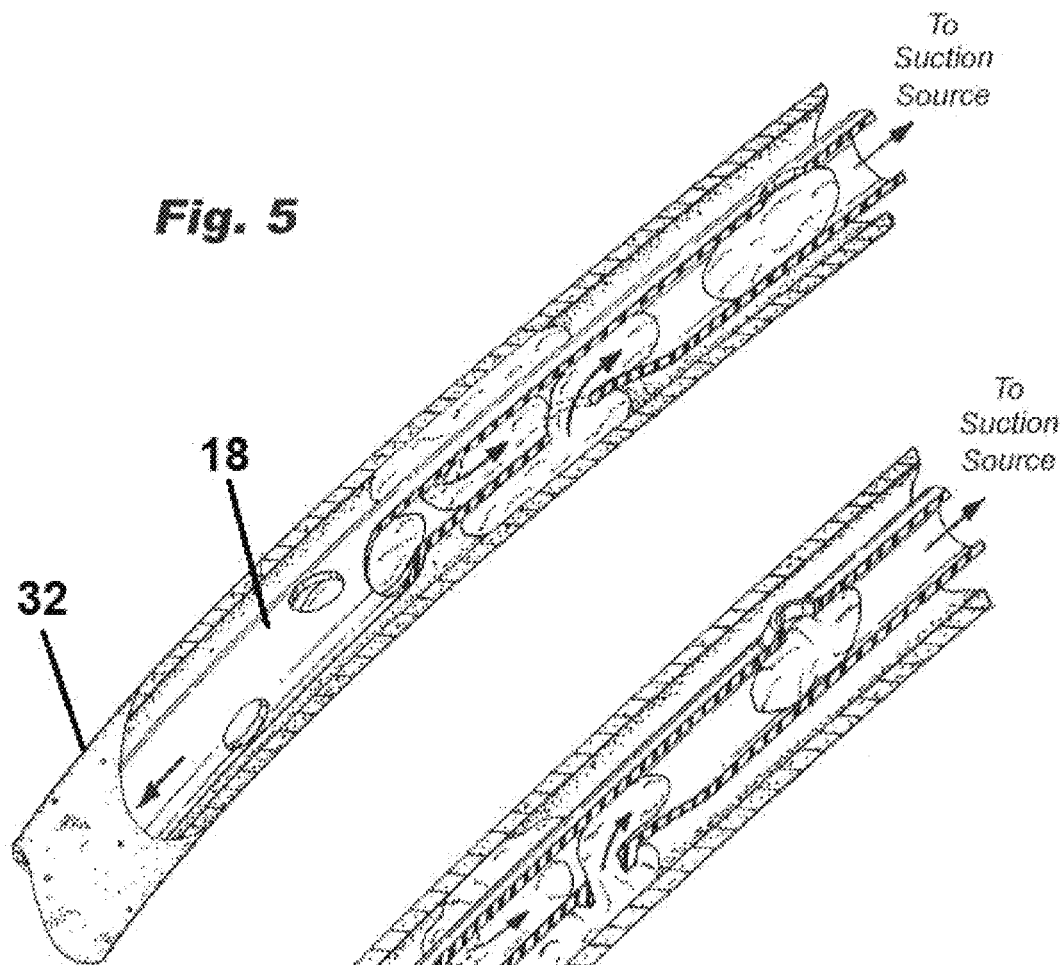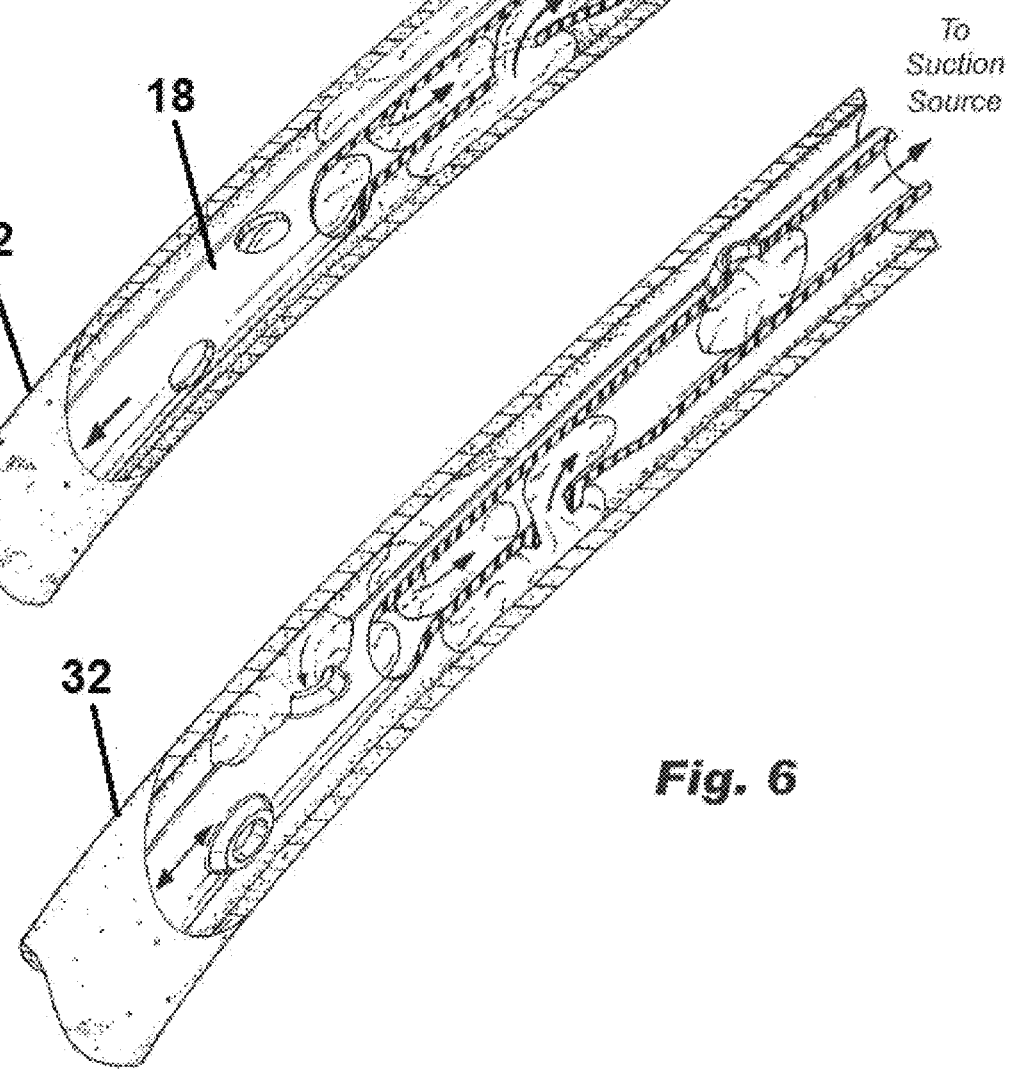

CATHETER FOR THROMBUS REMOVAL

This application claims priority from U.S. provisional patent application No. 63/017,773, filed on Apr. 30, 2020, which is incorporated herein in its entirety.

BACKGROUND

Removal of diseases, such as atherosclerotic plaque, thrombus, and other types of obstructions and partial obstructions from internal body lumens or cavities, is a well-established interventional technique. Many of the most common maladies affecting humans are caused by systemic arterial obstruction. The most common form of heart disease, such as myocardial infarction, results from thrombosis of a coronary artery following disruption of a cholesterol plaque. The most common causes of stroke include obstruction of a cerebral artery either from local thrombosis or thromboemboli, typically from the heart. Obstruction of the arteries to abdominal organs by thrombosis or thromboemboli can result in catastrophic organ injury, most commonly infarction of the small and large intestine. Obstruction of the arteries to the extremities by thrombosis or thromboemboli can result in gangrene.

In the systemic venous circulation, undesirable material can also cause serious harm. Blood clots can develop in the large veins of the legs and pelvis, a common condition known as deep venous thrombosis (DVT). DVT arises most commonly when there is a propensity for stagnated blood (long-haul air travel, immobility) and clotting (cancer, recent surgery, especially orthopedic surgery). DVT causes harm by obstructing drainage of venous blood from the legs leading to swelling, ulcers, pain and infection and serving as a reservoir for blood clot to travel to other parts of the body including the heart, lungs (pulmonary embolism) and across a opening between the chambers of the heart (patent *Foramen ovale*) to the brain (stroke), abdominal organs or extremities.

In the pulmonary circulation, the undesirable material can cause harm by obstructing pulmonary arteries, a condition known as pulmonary embolism. If the obstruction is upstream, in the main or large branch pulmonary arteries, it can severely compromise total blood flow within the lungs and therefore the entire body, resulting in low blood pressure and shock. If the obstruction is downstream, in large to medium pulmonary artery branches, it can prevent a significant portion of the lung from participating in the exchange of gases to the blood resulting in low blood oxygen and build up of blood carbon dioxide. If the obstruction is further downstream, it can cut off the blood flow to a smaller portion of the lung, resulting in death of lung tissue or pulmonary infarction.

There are numerous methods developed to treat blockages, such as clots and thrombus. Some of the most effective treatments for conditions resulting from the presence of blood clots or other undesirable materials within the circulation include stabilization or elimination of the material before it has embolized. Alternatively, if obstruction to flow has already occurred but before the obstruction has caused permanent harm (infarction, shock, death), the material can be eliminated by utilizing biologic or mechanical means.

Biologic treatments of such blockages involve the delivery of agents to the material, which either dissolve the material or, at a minimum, stabilize it until the body can eliminate it. In the case of infective vegetations, antimicrobial agents can, over time, decrease the chances of embolization. In the case of blood clots, the agents include 1) anticoagulant agents (heparin, warfarin, etc.), which prevent propagation of blood clots; and 2) more potent thrombolytic agents (streptokinase, urokinase, tPA, etc.), which actively dissolve clots. The agents are usually delivered systemically, i.e., into a peripheral or central vein and allowed to circulate throughout the body. Thrombolytic agents can also be delivered through a catheter directly to the blood clot which can increase its effectiveness by increasing local concentrations but this does not completely eliminate the absorption into systemic circulation throughout the body.

Thrombolytic agents have been shown to increase survival in patients with hemodynamically significant pulmonary embolism as documented by echocardiographic evidence of right ventricular strain. The use of thrombolytic agents is the standard of care in this subgroup of patients with a high 20-25% early mortality. They are commonly used in to dissolve clots in other blood vessels including arteries to heart, abdominal organs and extremities.

Mechanical treatments of such blockages involve the direct manipulation of the material to eliminate the obstruction. This can involve aspiration, maceration, and compression against the vessel wall, or other types of manipulation. The distinct advantage of mechanical treatment is that it directly attacks the offending material and eliminates the vascular obstruction independent of the specific content of the offending material. Mechanical treatments, if feasible, can usually prove to be superior to biologic treatments for vascular obstruction. Procedural success rates tend to be higher.

Numerous interventional catheters have been developed for such purpose. Most of these systems require placement of a guiding catheter and guide wire prior to introduction and placement of the interventional catheter at the target operating site. Advanceable and/or rotating operating heads have been used to cut and/or ablate obstructions. Many of these prior art systems incorporate aspiration systems to remove the ablated material from the site.

Other approaches include using thrombolytic therapy, which is the use of drugs to break up or dissolve blood clots. The most commonly used drug for thrombolytic therapy is tissue plasminogen activator (tPA). TPA is a thrombolytic or a "Clot Buster" drug. This clot buster is used to break-up the clot that is causing a blockage or disruption in the flow of blood, and helps restore the blood flow to the area of the brain. Another approach to thrombus removal is via a balloon catheter. Yet another approach includes mechanical thrombectomy with a stent retriever.

Another method of removing a thrombus utilizes an assembly, which includes a balloon catheter provided with two inflatable balloons which are spaced from one another at the distal end of the catheter. The balloon catheter is inserted endoluminally into the patient's vasculature until the balloons are located either side of a thrombus to be removed. The balloons are then inflated in order to close off the occluded part of the patient's vessel. The assembly includes provision for feeding into the space between the two inflated balloons a thrombolytic or other lytic agent, typically through a lumen of the balloon catheter. The thrombolytic agent will dissolve the thrombus located between the two inflated balloons, whereupon the dissolved thrombus material can be removed, typically by aspiration. Particularly when a thrombus is established, that is when the thrombus is dense and well set, it can take a significant time to dissolve the thrombus and thus remove this from the patient. Examples of thrombus treatment apparatus can be found, for example, in U.S. Pat. Nos. 5,279,546, 5,059,178 and 5,925,016.

Despite the many and varied approaches to material removal systems, many challenges remain in providing systems for removing material from a lumen, such as a blood vessel, safely and reliably and without causing complications. The safety and reliability of the system is manifestly critical. Recovery of debris generated during a material removal operation, or maceration of the debris to a particle size that will not produce blood vessel damage or embolic events is essential. The flexibility and size of an interventional catheter is also an important feature. The system must be small enough and flexible enough to navigate through sometimes tortuous internal structures and passageways, such as blood vessels, for placement at the target interventional site. The interventional catheter must also have sufficient stiffness and integrity to operate reliably at high rotational rates while allowing for aspiration and/or infusion of fluids to the site.

In interventional catheters that employ a "cutting head," any cutter structures must be benign during navigation of the operating head to and from the target site, yet effectively remove material during the operation. In addition, cutter structures must effectively remove disease or undesired material without damaging delicate neighboring tissue, such as blood vessel walls or other healthy tissue, which often surrounds the undesired material. Thus, it is important for cutter structures of the interventional catheter to accurately and reliably differentiate between the disease or undesired material and healthy tissue.

The extent and consistency of the disease or undesired material forming an obstruction are frequently not well characterized prior to an intervention. Thus, although interventional catheters and cutter assemblies having different sizes and material removal properties may be provided, and may even be interchangeable on a material removal system, it is difficult to ascertain which combination of features will be most effective in any particular intervention prior to insertion of the device. Various quick-connect systems have been developed to permit removal and installation of multiple operating catheters during a single surgical intervention. This is not ideal, since the interchange, requiring withdrawal and insertion of multiple interventional catheters, is time consuming and increases the risk of the operation. Having access to multiple cutter assemblies having different sizes and different material removal properties on a single interventional operating catheter is highly desirable.

Several prior art interventional catheters provide for aspiration of liquids and/or debris from the material removal site. In general, such aspiration is provided by a vacuum pump or, in many cases, by an evacuated recovery vessel, such as an evacuated bottle. These systems tend to provide inconsistent and variable vacuum during operation, which reduces the efficiency and effectiveness of the material removal operation and, under certain circumstances, may compromise the health of the patient.

There is a need in the art, therefore, for a catheter which can aspirate a thrombosis in an arteriovenous graft or fistula.

SUMMARY OF THE INVENTION

In accordance with the present invention, a catheter, a kit, and a method for removing a thrombus are provided. The catheter for removing a thrombus from the interior surface of a blood vessel includes a tubular body with a plurality of protrusions and apertures. The tubular body has a hollow interior, an exterior surface, a proximal end, and a distal end. The plurality of protrusions extends upwardly from the exterior surface and each protrusion has an aperture. The distal end of the catheter is inserted into the blood vessel and a suction is applied to the proximal end of the catheter to aspirate the thrombus from the blood vessel.

Each of the plurality of protrusions has a top surface and a perimetrical side wall extending between the top surface and the exterior surface of the catheter, wherein the aperture is in the top surface. Each protrusion has a cross-sectional dimension that is at least two times greater than a distance between the top surface of the protrusion and the exterior surface of the catheter. The plurality of protrusions includes at least two or more adjacent protrusions that can be located on opposite sides of the exterior surface of the catheter.

The maximum cross-sectional dimension of a least one of the apertures is about 1.5 millimeters to about 2.5 millimeters. Preferably, the apertures are separated by an average distance of about 4 millimeters to about 6 millimeters and are located between a mid-point of the catheter and the distal end.

The kit for removing a thrombus includes a catheter as described above, a suction device, and a mechanism for controlling and actuating the suction flow. The suction device is connected to the proximal end of the catheter and introduces a negative pressure and a suction flow into the catheter. The suction device is preferably a syringe. The mechanism is located between the proximal end of the catheter and the suction device for controlling and actuating the suction flow. The mechanism is preferably a manually operated valve. The catheter is inserted into the blood vessel and the suction device attached to the proximal end of the catheter provides a suction flow to aspirate the thrombus from the blood vessel. The mechanism is used to regulate the suction flow.

The method of removing a thrombus from a blood vessel in a mammal includes the steps of inserting a catheter, as described above, into the blood vessel and aspirating the thrombus by applying a suction to the distal end of the tubular body of the catheter to create a suction flow. The method can also include repeatedly inserting and partially withdrawing the catheter from the blood vessel to dislodge thrombus from an interior surface of the blood vessel before aspirating the thrombus. The step of applying a suction can include connecting a syringe having an actuator to the proximal end of the catheter and withdrawing the actuator to create the suction in the catheter. The method can also include a step for controlling the suction flow using a manually operated valve.

BRIEF DESCRIPTION OF THE DRAWINGS

The preferred embodiments of the catheter, kit and method for removing a thrombus of the present invention, as well as other objects, features and advantages of this invention, will be apparent from the accompanying drawings wherein:

FIG. 1 shows a catheter of the prior art.

FIG. 2 shows an overview of a first embodiment of the catheter of the present invention.

FIG. 3 shows the first embodiment of the catheter of the present invention in partial cross-section.

FIG. 4 shows a second embodiment of the catheter of the present invention in partial cross-section.

FIG. 5 shows the first embodiment of the catheter of the present invention as used in a vessel of a mammal.

FIG. 6 shows the second embodiment of the catheter of the present invention as used in a vessel of a mammal.

DETAILED DESCRIPTION OF THE PREFERRED EMBODIMENTS

Figure 7:
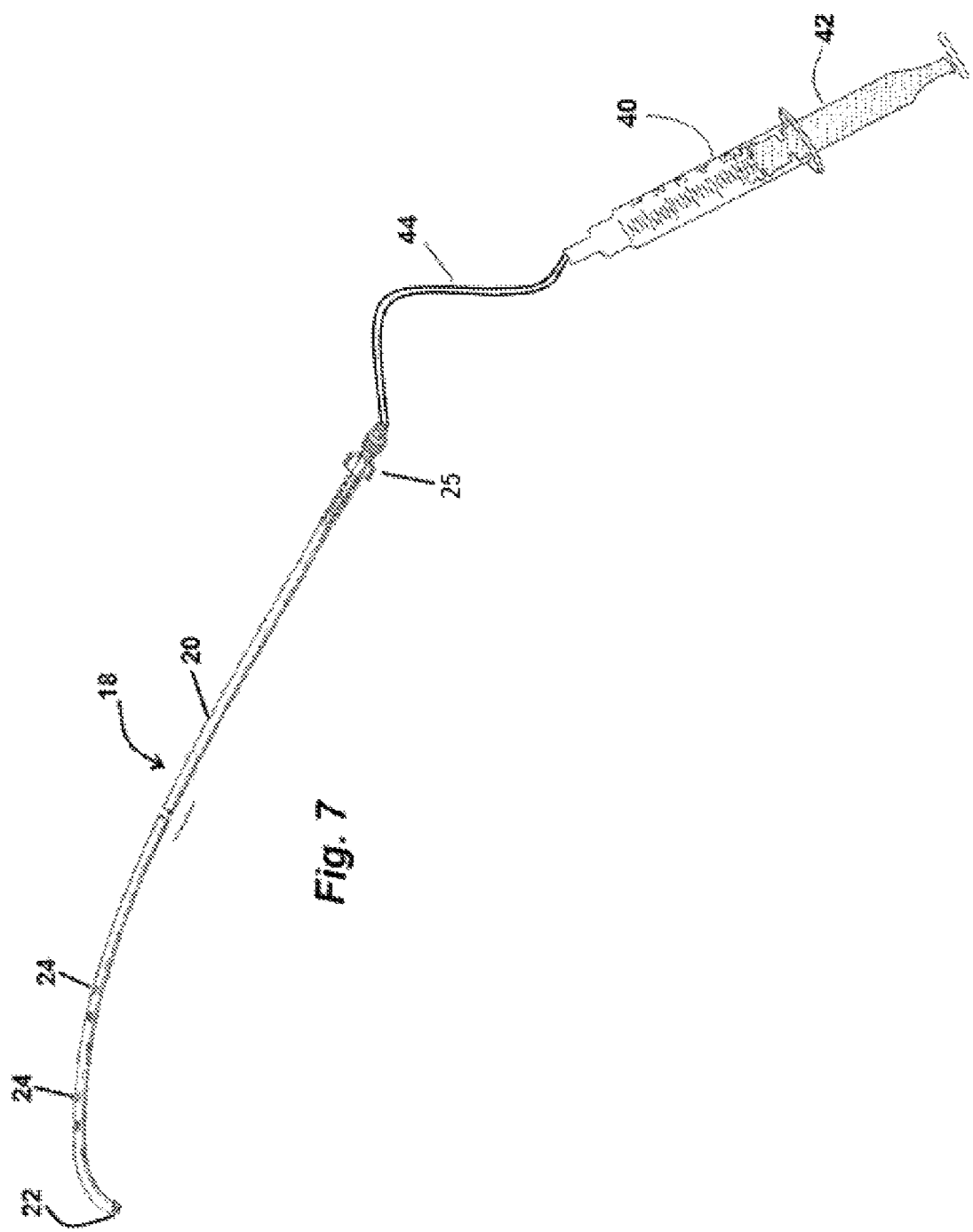
FIG. 7 shows the kit embodiment of the present invention, including the catheter, the mechanism for controlling the suction flow, and a syringe.

The following description discloses specific details in order to provide a thorough understanding of the invention. The skilled artisan, however, will understand that the invention can be practiced without employing all of these specific details. Indeed, the invention can be practiced by modifying the disclosed device and method and can be used in conjunction with apparatus and techniques conventionally used in the industry.

As used herein, the term "mammalian vessel" or "blood vessel" refers to a duct in the vascular system of the body through which blood flows.

As used herein, the term "thrombus" refers to a blood clot or other form of obstruction that forms on the interior wall of a blood vessel or in the heart when blood platelets, proteins, and cells stick together. A thrombus may reduce or block the flow of blood through the blood vessel.

As used herein, the terms "aspiration catheter" and "MECA" (Manual Endoluminal Clot Aspirator) catheter are used to refer to the catheter device of the present invention.

As used herein, the term "protrusion" refers to a portion of the exterior surface of a catheter that extends outwardly from the exterior surface in the form of a bump or a mound with a top surface and a perimetrical side wall that slopes downwardly from the top surface to the exterior surface of the catheter. The top surface has an aperture that provides a passage between the exterior of the catheter and the hollow interior of the catheter. The distance between the exterior surface of the catheter and the top surface and the extent of the top surface can vary.

The catheter of the present invention has a tubular body with an open distal end and a proximal end. The design and manufacture of such catheters is well known to those skilled in the art. When used, the distal end is inserted into a blood vessel and the proximal end is connected to a suction device, such as a syringe. The syringe has a hollow cylindrical chamber and an actuator that snugly fits into the chamber and provides suction (i.e., a negative pressure) in the catheter when withdrawn from the chamber. A plurality of apertures are located near the distal end of the catheter. The diameter of the tubular body of the catheter and the diameter and number of apertures are selected to provide the desired amount of suction applied to the interior surfaces of the blood vessel.

In a preferred embodiment, the tubular body of the catheter has a smooth exterior surface that facilitates insertion of the catheter into the blood vessel and its withdrawal therefrom and a plurality of protrusions with apertures extending outwardly from the exterior surface of the catheter. As described in more detail below, the protrusions are designed to contact and dislodge blood clots adhering to the interior surface of blood vessels so that they can be suctioned out. Typically, blood clots adhere to the interior walls of blood vessels and suction pressure alone is not sufficient to overcome the adherence. However, it has been found that the abrasion caused by the protrusions repeatedly passing over and contacting the blood clots allows the blood clots to be more easily and efficiently suctioned out of the blood vessel. The overall size of the protrusions depends primarily on the diameter of the aperture located in the protrusion, while the distance the protrusions extend from the exterior surface of the catheter depends on several factors including the inner diameter of the blood vessel and the outer diameter of the tubular body of the catheter. One skilled in the art would select the size and number of protrusions based on the individual patient and the specific application.

The multi side hole catheter design of the present invention facilitates the removal of thrombus as the aspiration catheter is pulled back in a retrograde fashion within the blood vessel. Continuous suction via an external syringe is applied to the aspiration catheter during thrombus removal. Increasing the number of apertures between the midpoint of the catheter and the distal end provides maximum thrombus aspiration within the blood vessel. However, in certain embodiments, the catheter has fewer apertures so that the suction pressure through the apertures during aspiration is increased. The suction pressure on the inner surface of the blood vessel is determined by the number of apertures in the catheter and the diameter of the apertures.

There are other catheters known in the art with side-wall apertures, but none meet the precise specifications of the presently claimed catheters, and none are used in the claimed methods. Boston Scientific markets the MACH 1™ Catheter, for example, which is used a guide catheter through renal veins, arteries, etc. Catheters such as these provide a pathway through which medical instruments, such as balloon dilatation catheters, guide wires or other therapeutic devices, may be introduced. These devices are not intended for use in the cerebral vasculature. These devices are also not designed or intended to be used for thrombus removal.

The catheter of present invention, on the other hand, is more effective in removing thrombus as compared to catheters because the protrusions dislodge thrombus from the interior walls of blood vessels and the apertures in the protrusions closely contact the interior walls. Preferably, the apertures have an oval shape and are placed near the tip of the catheter to maximize the evacuation of acute and chronic thrombi. When oscillated and drawn back in a retrograde manner, the catheter provides maximum dislodging of thrombi and aspiration through the plurality of strategically placed protruding apertures during a thrombectomy procedure.

Locating the apertures in protrusions allows a technique called "scraping therapy" to be implemented. Scraping therapy by definition is a manual form of therapy where an instrument is used to scrape over the skin and improve circulation in the area. Scraping therapy has been shown to aid in breaking down scar tissues that often result after some kind of trauma. Scraping therapy within blood vessels is used to atraumatically remove adherent, chronic, well organized thrombus from the vessel intima wall. This technique can require extrinsic compression as the MECA catheter is moved back and forth in a direction parallel to the longitudinal axis of the catheter, all while being attached to an external syringe for suction. The vessel wall apposition is maximized by the protrusions with raised apertures. Once separated from the interior wall of the blood vessel, the thrombi, or coagulated blood, can be easily evacuated from the arteriovenous (AV) graft or the venous outflow track of the AV fistula. This atraumatic design provides maximum adherent, chronic thrombus removal ensuring a level of outflow patency, which is essential for a successful thrombectomy procedure. Outflow drainage, either by normal anatomical vasculature or outflow vessel collateralization, as a result of chronic or acute vessel injury, is paramount for dialysis access function. All blood needs to be returned to the heart, regardless of the path it takes. Dialysis accesses have been proven to function at a high level with an indirect outflow; however, an outflow drainage track needs to exist or be established.

With reference now to the drawings, FIG. 1 shows a prior art thrombectomy catheter 10, which is longitudinally oriented with a sheath 12 extending between a distal tip 14 and a control handle or means 16. Extraction catheters of the prior art typically engage in thrombectomy procedures by a number of means including those listed in the background of this application.

With reference to FIG. 2 of the drawings, an aspiration catheter 18 of the present invention is shown. The aspiration catheter 18 includes a tubular body 20 extending between a distal tip 22 and a mechanism 25 for controlling and actuating the catheter 18 at a proximal end of catheter 18. Near the distal tip 22 of the catheter 18 is a plurality of apertures 24. The apertures 24 are preferably spaced about 4 to 6 mm apart from each other. The distal tip 22 may be radio-opaque. In a preferred embodiment, apertures 24 are spaced about 5 mm apart from each other. The apertures 24 in the tubular body 20 may be randomly spaced or may be arranged in an orderly configuration, such as rows horizontally arranged along the tubular body 20, or columns traversing the tubular body 20 circumferentially.

Referring to FIG. 3 of the drawings, a partial cross-section of catheter 18 is shown with the tubular body 20 cut away at portion 26. Cut-away portion 26 shows the side wall 28 of the catheter 18, which is preferably a double-braided construction.

FIG. 4 of the drawings shows a second embodiment of the present invention wherein the catheter 118 has a plurality of protrusions 132 extending outwardly from the exterior surface 121 of the tubular body 120. The protrusions 132 have a top surface 134 and a perimetrical side wall 136 extending between the top surface 134 and the exterior surface 121 of the tubular body 120. Each of the top surfaces 134 of the protrusions 132 has an aperture 130. The protrusions 132 dislodge thrombi adhering to the interior walls of blood vessels when the catheter 118 is inserted and partially withdrawn from the blood vessel a number of times. The dislodged thrombi are more easily removed from the patient through the apertures 130 in the catheter 118 when suction is applied and the blood vessel is aspirated.

FIGS. 5 and 6 show the catheter 18 in use in a blood vessel 32.

In a preferred embodiment, catheter 18 is used in a thrombus removal procedure using aspiration with a vacuum force suctioning out one or more thrombi. In one application of the catheter 18, thrombi are aspirated from a arteriovenous fistula. Vascular access failure is a crucial problem in chronic hemodialysis patients. Native arteriovenous fistulas (AVFs) and polytetrafluoroethylene (PTFE) grafts are used commonly for hemodialysis access. Autogenous AVFs are considered the vascular access of choice as defined by the National Kidney Foundation's Dialysis Outcomes Quality Initiative guidelines. Thrombosis is often caused either by associated vascular stenosis, which usually develops on the venous side of the shunt, or by venous thrombosis that occurs elsewhere in the same extremity, decreasing flow and increasing pressure. The vast majority of dysfunctional fistulas including stenosis and thrombosis of hemodialysis fistulas are treated by an interventional approach. Currently, percutaneous treatment regimens of thrombosed fistulas are mechanical thrombectomy, pharmaco-mechanical thrombolysis and infusion thrombolysis. Percutaneous recanalization of hemodialysis accesses have been described as a valuable alternative to surgical thrombectomy, either with the use of various thrombolytic drugs alone or in combination with dedicated percutaneous catheter-based devices.

The kit embodiment of the present invention is shown in FIG. 7 and it includes the catheter 18, as described in detail above, the mechanism 25 for controlling the suction flow and a syringe 40 connected to the catheter 18 by a tube 44. Withdrawing the actuator 42 of the syringe 40 creates a suction in the catheter 18 and withdraws blood as well as thrombi from the patient.

The present invention provides a catheter and method for aspirating thrombi. Such procedures are performed as follows. The art of a successful thrombectomy relies upon the process of debulking thrombus prior to pulling the arterial plug. The inventive catheter simplifies the process of debulking an arteriovenous graft and arteriovenous fistula. The multi side hole design allows for maximum thrombus removal via that similar to a pullback venogram. By placing the catheter ahead of the thrombus, attaching a 60 cc syringe utilizing counter suction will allow for maximum evacuation of thrombus in an arteriovenous graft and arteriovenous fistula. Once the catheter is successfully placed ahead of the thrombus, manual extrinsic compression could be applied to help facilitate the removal of the thrombus. All the while, reducing radiation exposure to the operator and intra operative personnel. The thrombi then evacuated can be expelled into a safety bowl for removal. The design of the catheter along with the flexibility allows for repeated use to maximize reduction of thrombi within the arterial venous graft and fistula. To evaluate the evacuation of thrombi, simply compress the inflow segments of the access and perform a venogram under slight pressure. Once maximum evacuation of thrombi has been achieved, the operator can then proceed with traditional thrombectomy measures. An advantage of the catheter of the present invention is that it simplifies debulking the access and allowing for maximum thrombectomy success. The present design provides optimal catheter diameter for removal of fresh and chronic thrombus. The inventive catheter can be used within the inflow segment of the arterial venous graft and arterial venous fistula up to the arterial plug when necessary.

Thus, while there have been described what are presently believed to be preferred embodiments of the invention, those skilled in the art will realize that changes and modifications may be made thereto without departing from the spirit of the invention, and it is intended to claim all such changes and modifications as fall within the true scope of the invention.

What is claimed is:

1. A catheter for removing a thrombus from the interior surface of a blood vessel, the catheter comprising:
   a tubular body having a hollow interior, an exterior surface, a proximal end, and a distal end; and
   a plurality of protrusions extending upwardly from the exterior surface, wherein each protrusion comprises an aperture, a top surface and a perimetrical side wall extending between the top surface and the exterior surface of the catheter, and wherein the aperture is in the top surface and the perimetrical side wall is circumferentially formed entirely around the aperture,
   wherein the distal end of the catheter is inserted into the blood vessel and a suction is applied to the proximal end of the catheter to aspirate the thrombus from the blood vessel.

2. The catheter according to claim 1, wherein each of the plurality of protrusions has a cross-sectional dimension that is at least two times greater than a distance between the top surface of the protrusion and the exterior surface of the catheter.

3. The catheter according to claim 1, wherein the plurality of protrusions includes at least two or more adjacent protrusions, and wherein the at least two or more adjacent protrusions are located on opposite sides of the exterior surface of the catheter.

4. The catheter according to claim 1, wherein a maximum cross-sectional dimension of at least one of the apertures is about 1.5 millimeters to about 2.5 millimeters.

5. The catheter according to claim 1, wherein the apertures are separated by an average distance of about 4 millimeters to about 6 millimeters.

6. The catheter according to claim 1, wherein the apertures are located between a mid-point of the catheter and the distal end.

7. A kit for removing a thrombus from the interior surface of a blood vessel, the kit comprising:
a catheter comprising:
a tubular body having a hollow interior, an exterior surface, a proximal end, and a distal end; and
a plurality of protrusions extending upwardly from the exterior surface, wherein each protrusion comprises an aperture, a top surface and a perimetrical side wall extending between the top surface and the exterior surface of the catheter, wherein the aperture is in the top surface and the perimetrical side wall is circumferentially formed entirely around the aperture,
wherein the distal end of the catheter is inserted into the blood vessel and a suction is applied to the proximal end of the catheter to aspirate the thrombus from the blood vessel;
a suction device connected to the proximal end of the catheter, wherein the suction device introduces a negative pressure and a suction flow into the catheter; and
a mechanism located between the proximal end of the catheter and the suction device for controlling and actuating the suction flow.

8. The kit according to claim 7, wherein each of the plurality of protrusions has a cross-sectional dimension that is at least two times greater than a distance between the top surface of the protrusion and the exterior surface of the catheter.

9. The kit according to claim 7, wherein the plurality of protrusions includes at least two or more adjacent protrusions, and wherein the at least two or more adjacent protrusions are located on opposite sides of the exterior surface of the catheter.

10. The kit according to claim 7, wherein the maximum dimension of at least one of the apertures is about 1.5 millimeters to about 2.5 millimeters, wherein the apertures are separated by an average distance of about 4 millimeters to about 6 millimeters, and wherein the apertures are located between a mid-point of the catheter and the distal end.

11. The kit according to claim 7, wherein the suction device is a syringe.

12. The kit according to claim 7, wherein the mechanism for controlling and actuating the suction flow is a manually operated valve.

13. A method of removing a thrombus from a blood vessel in a mammal, the method comprising:
inserting a catheter into the blood vessel of the mammal, wherein the catheter comprises:
a tubular body having a hollow interior, an exterior surface, a proximal end, and a distal end; and
a plurality of protrusions extending upwardly from the exterior surface, wherein each protrusion comprises an aperture, a top surface and a perimetrical side wall extending between the top surface and the exterior surface of the catheter, wherein the aperture is in the top surface and the perimetrical side wall is circumferentially formed entirely around the aperture; and
aspirating the thrombus by applying a suction to the distal end of the tubular body of the catheter to create a suction flow.

14. The method according to claim 13, wherein the catheter is repeatedly inserted and partially withdrawn from the blood vessel of the mammal to dislodge a thrombus from an interior surface of the blood vessel before aspirating the thrombus.

15. The method of claim 13, wherein the aspirating comprises connecting a syringe having an actuator to the proximal end of the catheter and withdrawing the actuator to create the suction in the catheter.

16. The method of claim 13, wherein a maximum cross-sectional dimension of at least one of the apertures is about 1.5 millimeters to about 2.5 millimeters.

17. The method according to claim 13, wherein the plurality of protrusions includes at least two or more adjacent protrusions, wherein the at least two or more adjacent protrusions are located on opposite sides of the exterior surface of the catheter, and wherein the maximum dimension of at least one of the apertures is about 1.5 millimeters to about 2.5 millimeters, and wherein the apertures are located between a mid-point of the catheter and the distal end.

18. The method according to claim 13, wherein a syringe is used to provide the suction, and wherein the suction flow is controlled by a manually operated valve.

* * * * *